(12) United States Patent
Mirshekari et al.

(10) Patent No.: US 10,653,868 B2
(45) Date of Patent: May 19, 2020

(54) DEVICE FOR SHAPING A GUIDEWIRE

(71) Applicant: Les Solutions Medicales Soundbite Inc., Saint-Laurent (CA)

(72) Inventors: Gholamreza Mirshekari, Sherbrooke (CA); Louis-Philippe Riel, Montreal (CA); Maude Laforest, Quebec (CA); Domenic Santoianni, Kirkland (CA); Martin Brouillette, Sherbrooke (CA)

(73) Assignee: Les Solutions Medicales Soundbite Inc., Saint-Laurent, Quebec (CA)

(*) Notice: Subject to any disclaimer, the term of this patent is extended or adjusted under 35 U.S.C. 154(b) by 0 days.

(21) Appl. No.: 15/837,605

(22) Filed: Dec. 11, 2017

(65) Prior Publication Data
US 2018/0161548 A1    Jun. 14, 2018

Related U.S. Application Data

(60) Provisional application No. 62/432,925, filed on Dec. 12, 2016.

(51) Int. Cl.
*A61M 25/09* (2006.01)

(52) U.S. Cl.
CPC .......... *A61M 25/09016* (2013.01); *A61M 25/09041* (2013.01); *A61M 2025/09108* (2013.01)

(58) Field of Classification Search
CPC .. A61M 25/09041; A61M 2025/09116; A61M 25/09016; A61M 25/09; A61M 2025/09108; B21F 1/002
See application file for complete search history.

(56) References Cited

U.S. PATENT DOCUMENTS

| | | | | |
|---|---|---|---|---|
| 3,854,583 A * | 12/1974 | Amberg | ................ | B29C 61/025 206/520 |
| 4,716,757 A * | 1/1988 | McGregor | ...... | A61M 25/09041 140/106 |
| 5,003,990 A * | 4/1991 | Osypka | ................. | A61M 25/01 600/585 |
| 5,277,231 A * | 1/1994 | Dostalek | ........... | A61M 25/0009 140/106 |
| 2011/0030193 A1* | 2/2011 | Adams | ..................... | B21D 5/16 29/505 |

FOREIGN PATENT DOCUMENTS

GB        1013648        * 12/1965    ............ B21D 7/063

* cited by examiner

*Primary Examiner* — Rene T Towa
(74) *Attorney, Agent, or Firm* — Taft Stettinius & Hollister LLP

(57) ABSTRACT

There is described a tip shaping device for shaping a tip of a guidewire, including an elongated body extending along a longitudinal axis between two end faces and having a lateral face extending along the longitudinal axis between the two end faces; and a planar body projecting from the lateral face of the elongated body, the planar body including a flexible section located adjacent to the elongated body and wrappable around at least a portion of the lateral face of the elongated body, the planar body having a guidewire receiving face adapted to shape the guidewire when received thereon and upon rotation of the elongated body over the planar body.

20 Claims, 3 Drawing Sheets

DEVICE FOR SHAPING A GUIDEWIRE

CROSS REFERENCE TO RELATED APPLICATIONS

The present application claims the benefit of U.S. Provisional Application No. 62/432,925 filed Dec. 12, 2016, the contents of which are incorporated herein in their entirety.

TECHNICAL FIELD

The present invention relates to the field of medical guidewires, and more particularly to devices for shaping guidewires.

BACKGROUND

Guidewires are fine wires that are used to navigate through the vasculature of a body to gain access to various tissues and organs through a small skin opening. Guidewires are navigated by pushing, pulling and rotating the wire around its longitudinal axis. To improve navigability, it is often desirable that the distal tip of the guidewire be shaped, over a given length such as a length ranging from 0.25 mm to a few centimeters from the distal tip, according to the requirements of a physician operator.

Usually the tip of the guidewire is shaped by inserting the distal tip into a needle introducer device, or any other small tube, and subsequently bending the desired guidewire region by hand. This is performed during a procedure, on an as-needed basis by the physician operator. Because the guidewire tip is shaped by hand, such a bending method may suffer from poor reproducibility and risks introducing shapes that are deleterious to the mechanical integrity of the guidewire.

Some tip shaping devices have been developed to alleviate these shortcomings, but some of them are too mechanically complex for widespread clinical use.

Therefore, there is a need for an improved guidewire tip shaping device for shaping a guidewire.

SUMMARY

According to a first broad aspect, there is provided a tip shaping device for shaping a tip of a guidewire, comprising: an elongated body extending along a longitudinal axis between two end faces and comprising a lateral face extending along the longitudinal axis between the two end faces; and a planar body projecting from the lateral face of the elongated body, the planar body comprising a flexible section located adjacent to the elongated body and wrappable around at least a portion of the lateral face of the elongated body, the planar body comprising a guidewire receiving face adapted to shape the guidewire when received thereon and upon rotation of the elongated body over the planar body.

In one embodiment, the tip shaping device further comprises a stopper body extending from the lateral face of the elongated for limiting a rotation of the elongated body over the planar body.

In one embodiment, the stopper body is provided with one of a square, rectangular and triangular cross-sectional shape.

In one embodiment, the planar body is provided with at least one groove on the guidewire receiving face for receiving the guidewire therein.

In one embodiment, the elongated body is provided with at least one hole each facing a respective one of the at least one groove for receiving the guidewire therein.

In one embodiment, the at least one groove is provided with groove ridges.

In one embodiment, the elongated body is provided with at least one bump each extending along the lateral face thereof, each one of the at least one bump being aligned with a respective one of the at least one groove upon wrapping of the planar body over the elongated body.

In one embodiment, the bump is provided with bump ridges.

In another embodiment, the lateral face of the elongated body is provided with at least one groove for receiving therein the guide wire.

In one embodiment, the planar body is provided with at least one hole each facing a respective one of the at least one groove for receiving the guidewire therein.

In one embodiment, the at least one groove is provided with groove ridges.

In one embodiment, the planar body is provided with at least one bump each extending along the guidewire receiving face, each one of the at least one bump being aligned with a respective one of the at least one groove upon wrapping of the planar body over the elongated body.

In one embodiment, the bump is provided with bump ridges.

In one embodiment, a cross-sectional dimension of the elongated body varies along a longitudinal axis thereof.

In one embodiment, a shape of the elongated body varies along a longitudinal axis thereof.

In one embodiment, the guidewire receiving face is a face of the planar body that is in contact with the elongated body upon wrapping of the planar body over the elongated body.

In one embodiment, the guidewire receiving surface is a lateral face.

In one embodiment, the tip shaping device further comprises a finger receiving loop secured at a junction between the elongated body and the planar body.

In one embodiment, the elongated and planar bodies are made of a biocompatible and sterilizable material.

In one embodiment, the guidewire receiving face of the planar body is coated with one of a hydrophilic, hydrophobic and friction-reducing coating.

In one embodiment, the elongated body is provided with one of a circular, an elliptical, a square, a rectangular, a hexagonal and a clothoid cross-sectional shape.

In one embodiment, the tip shaping device further comprises a lever projecting from a lateral face of the elongated body for rotating the elongated body.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
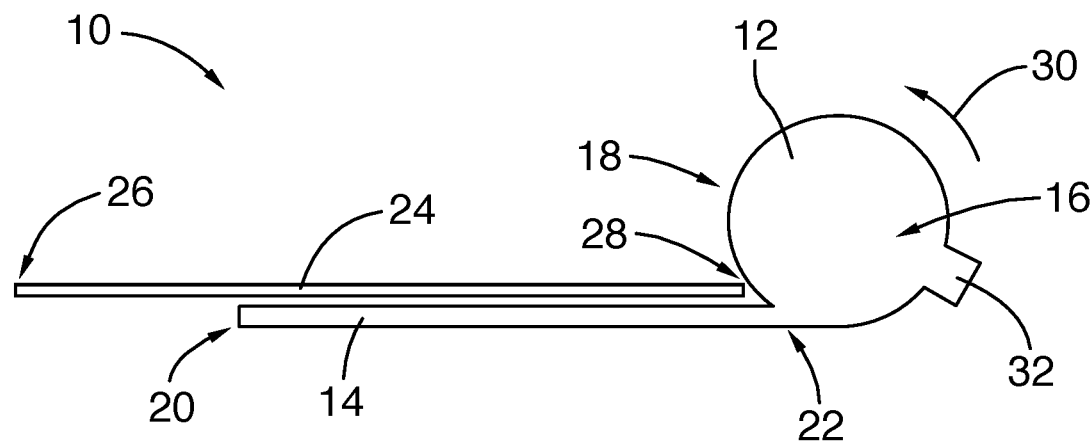
FIG. 1 is a side view of a tip shaping device comprising a cylindrical mandrel and a flexible flap with a guidewire positioned on the flap, in accordance with an embodiment.

FIG. 1 illustrates one embodiment of a tip shaping tool or device 10. The tool 10 comprises a mandrel 12 and a flexible flap 14 which protrudes from the cylindrical mandrel 12. In the illustrated embodiment, the mandrel 12 has a cylindrical shape and extends along a longitudinal axis. The mandrel 12 comprises two opposite disk-shaped end faces 16 which are substantially orthogonal to its longitudinal axis and a lateral face 18 which extends between the two opposite end faces 16.

The flexible flap 14 protrudes from the lateral face 18 of the mandrel 12 and comprises a plate which extends between a proximal end 20 and a distal end 22 within a plane. In one embodiment, the plane within which the flexible flap 14 extends is parallel to the longitudinal axis of the mandrel 12. In another embodiment, the plane within which the flexible flap 14 extends contains the longitudinal axis of the mandrel 12. In a further embodiment, the plane within which the flexible flap 14 extends intersects the longitudinal axis of the mandrel 12.

The flexible flap 14 is made of a flexible material which allows the flexible flap 14 to be wrapped at least partially around the mandrel 12. For example, the flexible flap 14 may be made of rubber, silicon or any other adequate substantially flexible material.

In order to shape a guidewire 24 extending longitudinally between a proximal end 26 and a distal end 28 using the tip shaping device 10, the guidewire 24 is positioned on top of the flexible flap 14 so that its distal end 28 be adjacent to the lateral face 18 of the mandrel 12 or abuts against the lateral face 18 of the mandrel 12. Then the mandrel 12 is rotated about its longitudinal axis according to a first rotation direction 30 towards the flexible flap 14 so as to wrap the flexible flap 14 at least partially around the lateral face 18 of mandrel 12. During the rotation of the mandrel 12, at least the section of the flexible flap 14 adjacent to the distal end 22 thereof is deformed and the deformed section of the flexible flap 14 takes substantially the same shape as that of the lateral face 18 of the mandrel 12. During the rotation of the mandrel 12, the section of the guidewire 14 adjacent to its distal end 28 becomes sandwiched between the lateral face 18 of the mandrel 12 and the flexible flap 14. As a result, the sandwiched section of the guidewire 14 is deformed during the rotation of the mandrel 12 while wrapping around the lateral face 18 of the mandrel 12 to take a different shape that depends on the shape of the lateral face 18 of the mandrel 12. As the guidewire 24 is bent between the mandrel 12 and the flexible flap 14, plastic deformation of the guidewire 24 takes place, resulting in a permanent deformation of the guidewire 24 in a shape that is controlled by the geometry of the lateral face 18 of the mandrel 12.

Once the mandrel 12 has been rotated about a desired rotation angle which corresponds to a desired length over which the guidewire 24 is to be shaped, the mandrel 12 is rotated about its longitudinal axis in a second rotation direction that is opposite to the first rotation direction or the flexible flap 14 is unwrapped from the mandrel 12.

In one embodiment, rotating the mandrel 12 according to the second rotation direction or unwrapping the flexible flap 14 from the mandrel 12 may be sufficient to remove the shaped guidewire 24 from the assembly.

In another embodiment, the guidewire 24 may be secured to the mandrel after rotating the mandrel 12 according to the second rotation direction or unwrapping the flexible flap 14 from the mandrel 12. In this case, the guidewire 24 may be removed from the mandrel 12 by sliding the guidewire 24 along the longitudinal axis of the mandrel 12 in direction of one of the two end faces 16.

Figure 2:
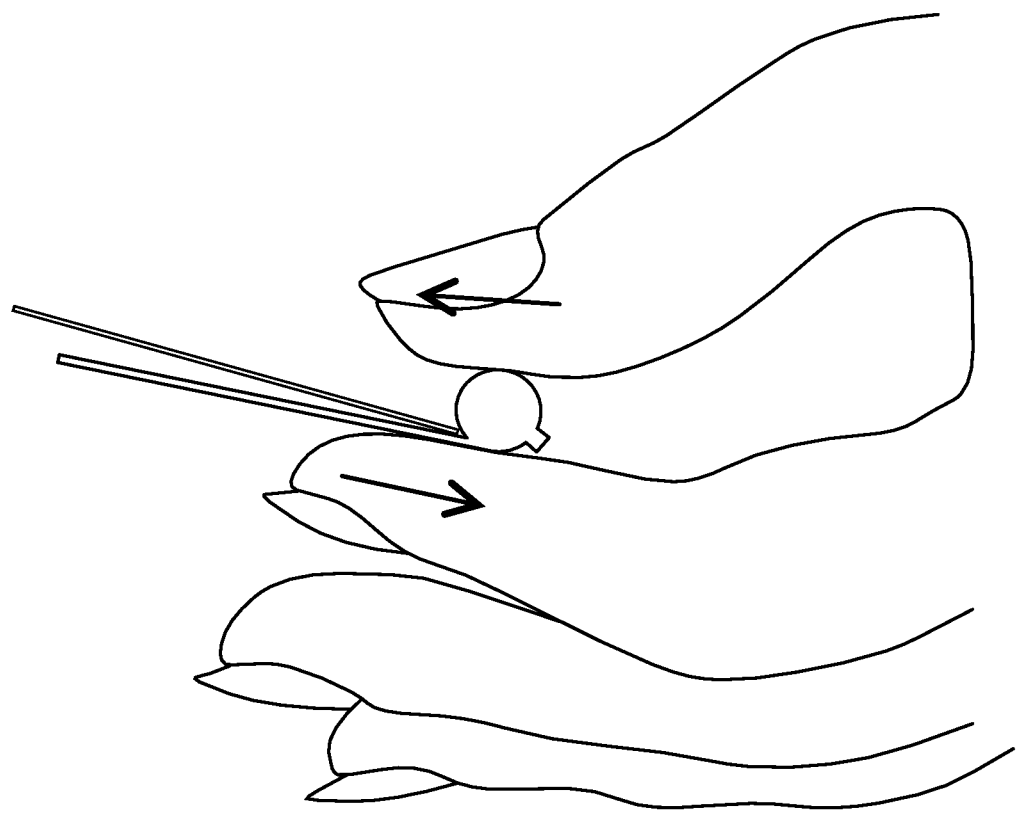
FIG. 2 illustrates the tip shaping device of FIG. 1 while in use, in accordance with an embodiment.

As illustrated in FIG. 2, the rotation of the mandrel 12 in the first rotation direction can be achieved by placing the tip shaping device 10 between the thumb and the index finger of a hand, the index finger being in contact with the flexible flap 14 and the thumb being in contact with the side of the mandrel 12 that is opposite to the flexible flap 14. By moving the thumb and the index finger in opposite directions as illustrated in FIG. 2, the flexible flap 14 may be wrapped around the mandrel 12, thereby shaping at least the distal end section of the guidewire 24.

In one embodiment, the tip shaping device 10 is further provided with a stopper 32 which protrudes from the lateral surface 18 of the mandrel 12 at a given angular position along the lateral face 18 away from the distal end 22 of the flexible flap 14. The stopper 32 is used for limiting the rotation of the mandrel 12 about its axis and thereby limiting the length of the guidewire that will be deformed during the rotation of the mandrel 12. The relative angular position between the stopper 32 and the point of the lateral surface 18 of the mandrel from which the flexible flap 14 protrudes defines the length along which the guidewire 24 will be deformed and shaped.

While in the illustrated embodiment, the stopper 32 has a substantially square shape, it should be understood that any adequate shape that prevents the rotation of the mandrel 12 when the stopper 32 abuts against the flexible flap 14 may be used. For example, the stopper 32 may be provided with a rectangular or a triangular cross-sectional shape.

In one embodiment, the stopper 32 may be omitted and the tip shaping device 10 may be provided with at least one visual indicator positioned on at least one of the end faces 16. The visual indicator is then positioned at an adequate angular position along the circumference of the end face 16 and the adequate position may be chosen as a function of a desired length over which the guidewire 24 is to be bent. In one embodiment, the mandrel 12 may be provided with at least two visual indicators positioned at different angular positions along the circumference of the end face 16 in order to indicate predetermined and different lengths over which the guidewire 24 may be bent. In a further embodiment, the visual indicator may correspond to a visual graded scale which allows a user to choose a desired length for bending the guidewire 24.

In another embodiment, the rotation of the mandrel 12 and wrapping of the flexible flap 14 around the mandrel 12 can be achieved by providing the flap 14 with a non-flexible section. For example, the section of the flap 14 that is adjacent to the mandrel 12 may be flexible while the section of the flap 14 that is away from the mandrel 12 may be rigid or non-flexible. In this case, the rotation of the mandrel 12 is limited by the length of the flexible section of the flap 14 since the rigid section of the flap 14 cannot be wrapped around the mandrel 12. The length of the flexible section defines the maximum length over which the guidewire 24 may be bent.

In another example, the flap 14 may be made of a flexible material and a rigid plate may be secured to the flap 14 away from the mandrel 12. The rigid plate may be secured on top or below the flap 14. The section of the flap 14 that is not covered by the rigid plate can be wrapped over the mandrel 12 while the section of the flap 14 that is covered by the rigid plate cannot be wrapped over the mandrel 12. It should be understood that the length of the section of the flap 14 which is not secured to the rigid plate corresponds to the maximum length over which the guidewire 24 may be bent.

In one embodiment, providing the tip shaping device 10 with a rotation limiting device such as the stopper 32 allows shaping the tip of the guidewire 24 in a controlled and repeatable manner.

It should be understood that the shape of the deformed section of the guidewire 24 is set by the shape of the lateral face 18 of the mandrel 12. Therefore, a desired shape for the guidewire tip can be obtained by adequately choosing the shape of the lateral face 18 and the size and shape of the cross-section of the mandrel 12. For example, the cross-section of the mandrel 12 may have a circular shape, an elliptical shape, a clothoid shape, a square shape, a rectangular shape, a hexagonal shape or the like.

It should be understood that the mandrel 12 has adequate dimensions and/or is made of a sufficiently rigid material so that the guidewire 24 may deformed while the mandrel 12 is rotated.

Figure 3:
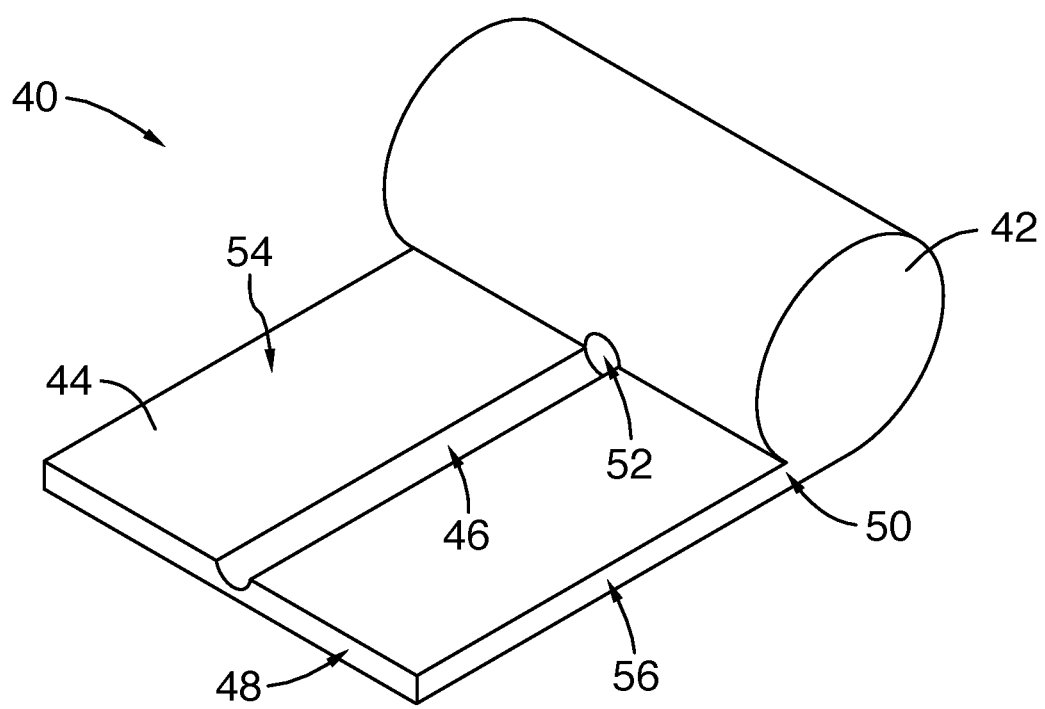
FIG. 3 illustrates a tip shaping device comprising a cylindrical mandrel and a flexible flap provided with a groove extending therealong; the cylindrical mandrel being provided with a hole facing the groove of the flexible flap, in accordance with an embodiment.

FIG. 3 illustrates another embodiment for a tip shaping device 40 which comprises a mandrel 42 and a flexible flap 44 which projects from the lateral face of the mandrel 42. In this embodiment, the flexible flap 44 is provided with a groove 46 which extends along the length of the flexible flap 44 from its proximal end 46 to its distal end 50 orthogonal to the axis of the mandrel 42. The groove 46 is shaped and sized for receiving a guidewire therein. For example, the groove 46 may have a hemi-cylindrical shape. In order to modify the shape of the distal end of a guidewire, the guidewire is inserted into the groove 46 and the distal end of the guidewire is positioned adjacent to the mandrel 42 or in physical contact the mandrel 42, and the mandrel 42 is rotated over the flexible flap 44. The groove 46 ensures that the guidewire does not substantially move transversally during the rotation of the mandrel 42 over the flap 44.

While in the illustrated embodiment the groove 46 extends along a longitudinal axis which is substantially orthogonal to the longitudinal axis of the mandrel 42, it should be understood that other configuration may be possible. For example, the groove 46 may extend along a longitudinal axis which forms an angle with the longitudinal axis of the mandrel that is other than 90 degrees. In one embodiment, the tip shaping device 40 may be provided with more than one groove 46 on the flap 44. For example, the grooves may have different dimensions and/or shape so that a same tip shaping device 40 may be used for shaping guidewires having different dimensions and/or shape. In another example, the grooves may extend along longitudinal axes which form different angles with the longitudinal axis of the mandrel 42 so that a same tip shaping device 40 may provide different shapes for guidewires.

While in the illustrated embodiment the groove 46 extends along the whole length of the flap 44, it should be understood that the groove 46 may extend only along a section of the flap that is adjacent to the mandrel 42.

In one embodiment, the mandrel 42 is further provided with a hole 52 that faces the groove 46 so that a guidewire positioned in the groove 46 may be inserted into the hole 52 in order to ensure that the distal end of the guidewire which is inserted into the hole 52 cannot substantially move during the rotation of the mandrel 42. It should be understood that if the tip shaping device 40 comprises more than one groove, each groove may be provided with a respective hole in the mandrel 42.

In one embodiment, the hole 52 extends along only a section of the mandrel 42. In this case, the distal section of the guidewire may be bent. In another embodiment, the hole 52 may extend along the whole width (or diameter) of the mandrel 42. In this case, the bending of the guidewire is not limited to its distal end and any adequate section of the guidewire may be bent by inserting the guidewire through the hole and translating the guidewire until the section to be bent be adjacent to the proximal end of the hole.

While the groove 46 is located on the top face 54 of the flap 44, i.e., the face of the flap 44 which is in physical contact with the mandrel 42 upon rotation of the mandrel 42 over the flap 44, it should be understood that the groove 46 could be located on a lateral face 56 of the flap 44. Such a configuration may help in properly locating the guidewire tip and prevent slipping during use. Alternatively, the groove 46 could be located on the bottom face of the flap 44, i.e., on the face opposite to the flap face that is to be in physical contact with the mandrel 42 upon rotation of the mandrel 42 over the flap 44.

While in the above description, the flap is provided with a groove on its top, bottom or lateral face, it should be understood that the flap may be provided with a hole extending within the thickness of the flap from its front or proximal face towards the mandrel for receiving therein a guidewire to be shaped. The cross-sectional shape and dimension of the guidewire receiving hole are chosen as a function of those of the guidewire to be received therein. The guidewire is then inserted into the hole until the distal end of the guidewire abuts against the end of the hole, and the mandrel is rotated in order to bend the distal section of the guidewire.

It should be understood that the groove could be located on the mandrel 42 instead of the flap. In this case, the groove extends along at least a section of the circumference of the lateral face of the mandrel 42. In this case, the flap 44 may be provided with a hole for receiving the tip of the guidewire.

Figure 4:
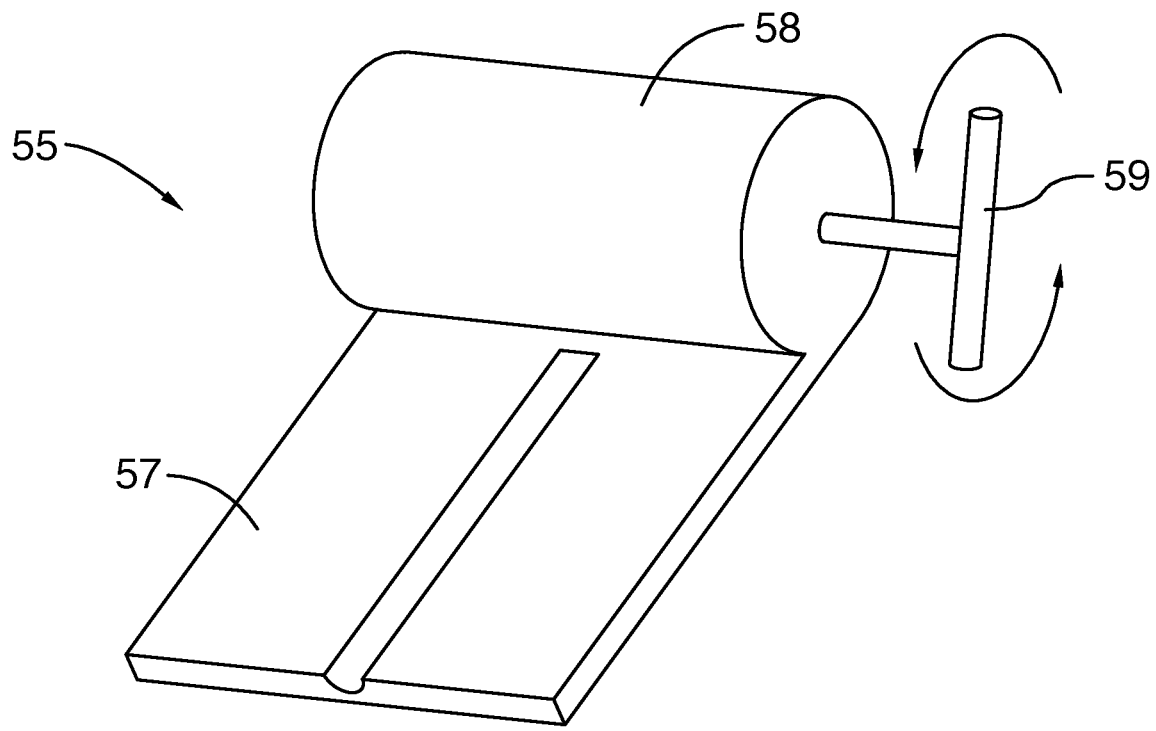
FIG. 4 illustrates a tip shaping device comprising a cylindrical mandrel, a flexible flap and a lever projecting from a lateral face of the mandrel, in accordance with an embodiment.
Figure 5:
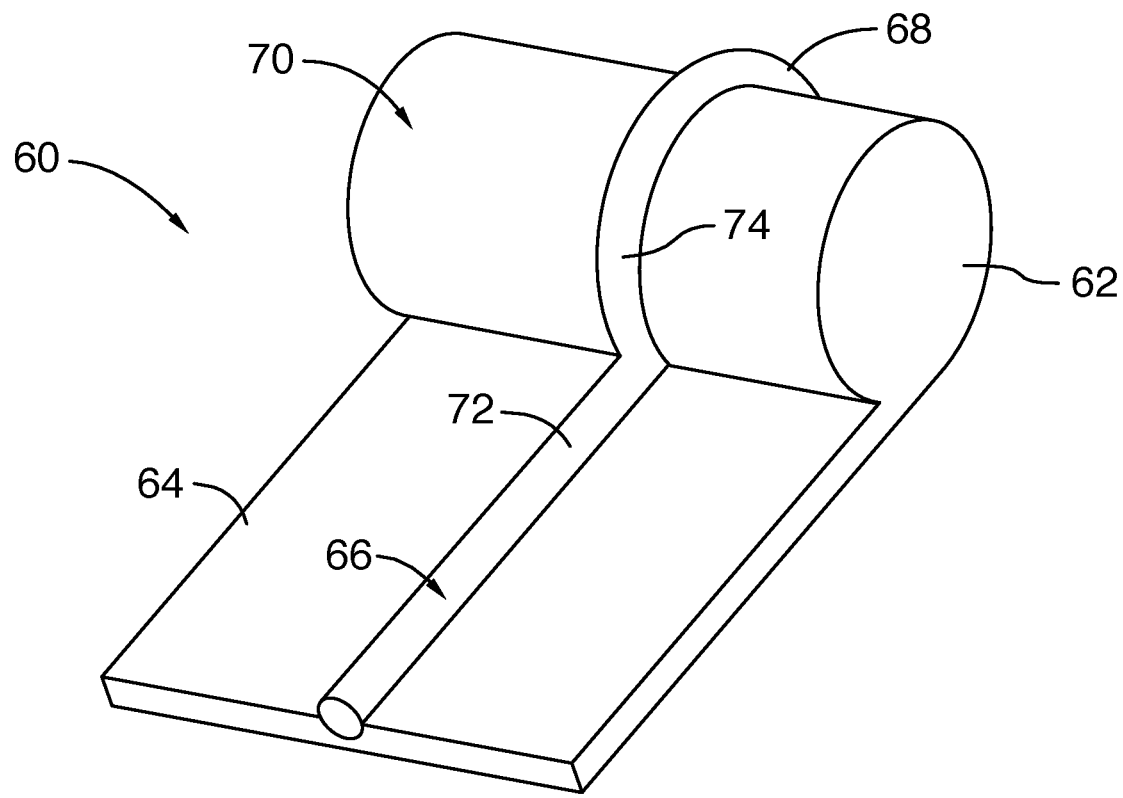
FIG. 5 illustrates a tip shaping device comprising a cylindrical mandrel provided with a bump, and a flexible flap provided with a groove, in accordance with an embodiment.

FIG. 4 illustrates one embodiment of a tip shaping device 55 comprising a flexible flap 57, a mandrel 58 and a lever or key 59 projecting from a lateral face of the mandrel 58. The guidewire is then bent by twisting the lever 59 in order to rotate the mandrel 58 and therefore bend the guidewire. In one embodiment, the use of the lever 59 improves the repeatability of the bending of guidewires in comparison to the case in which fingers are used for rotating a mandrel. FIG. 5 illustrates a further embodiment of a tip shaping device 60 which comprises a mandrel 62 and a flexible flap 64 adapted to be wrapped around the mandrel 62 upon a rotation on the mandrel 62 around its longitudinal axis and over the flexible flap 64. The flap 64 is provided with a groove 66 for receiving therein a guidewire to be shaped. The mandrel 62 comprises a bump or protrusion 68 which projects from the lateral face 70 of the mandrel 62. The bump 68 extends along at least a section of the lateral face 70 of the mandrel 62 and is positioned to face the groove 66 so that the bump 68 be received in the groove 66 when the flap 64 is wrapped over the mandrel and no guidewire is inserted into the groove 66. The bump 66 allows solidly wedging a guidewire inserted into the groove 66 between the mandrel 62 and the flap 64 during the rotation of the mandrel 62 over the flap 64.

In another embodiment, the tip shaping device is part of a tip shaping system comprising a stationary frame adapted to rotatably receive the mandrel of the tip shaping device. In this case, the mandrel comprises two cylindrical protrusions each extending from a respective lateral face thereof and superimposed with the axis of rotation of the mandrel. The stationary frame comprises two arms each for receiving a respective cylindrical protrusion which may rotate relative to the arm in which it is received. In one embodiment, at least one of the two cylindrical protrusions corresponds to a lever such as lever 59 for rotating the mandrel relative to the stationary frame.

While the groove 66 is provided on the flap 64 and the bump 68 is provided on the mandrel 62, it should be understood that the reverse configuration may be possible. i.e., the groove may be located on the mandrel and the bump may be provided on the flap.

In one embodiment, the groove 66 and the bump 68 are provided with ridges 72 and 74, respectively, to further increase the frictional resistance between the guidewire and the tip shaping device 60 during the rotation of the mandrel 62 over the flap 64. In one embodiment the ridges 72 and 74 are mating counterparts that fit into each other in the absence of a guidewire. In one embodiment the ridges 72 and 74 are mating gear-like features.

Figure 6:
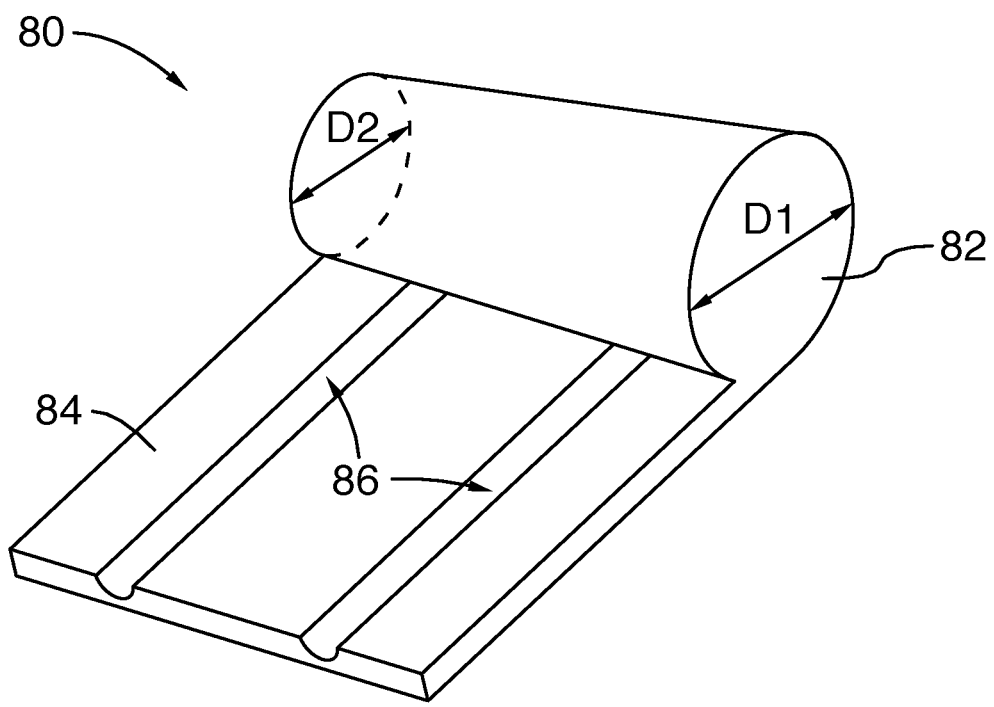
FIG. 6 illustrates a tip shaping device comprising a cylindrical mandrel and a flexible flap, the cylindrical mandrel having a varying diameter, in accordance with an embodiment.

FIG. 6 illustrates a tip shaping device 80 which comprises a mandrel 82 and a flexible flap 84 adapted to be wrapped around the mandrel 82 upon a rotation on the mandrel 82 around its longitudinal axis and over the flexible flap 84. While in the above embodiments, the mandrel 12, 42, 62 has constant cross-sectional dimensions, the mandrel 82 has a tubular shape extending along a longitudinal axis of which the cross-section dimension, e.g., the diameter, varies along the longitudinal axis. In the illustrated embodiment, the mandrel has a maximum diameter D1 at a first end along its longitudinal axis and a minimum diameter D2 at the opposite end along its longitudinal axis. Such a mandrel 82 provided with a varying cross-sectional dimension allows providing different shapes to a guidewire depending on the position of the guidewire tip along the longitudinal axis of the mandrel 82.

In one embodiment, the flap 84 is provided with grooves 86 which are each positioned at a respective position along the longitudinal axis of the mandrel 82 so that each groove 86 provides a respective shape for a guidewire when inserted therein.

In one embodiment, the shape of the lateral face of a mandrel, i.e., the cross-sectional shape of the mandrel, may vary along the longitudinal axis so that different shapes may be provided to guidewires while using a same mandrel.

In one embodiment, the lateral face of the mandrel and/or the flap is provided with surface roughness elements in order to improve the grip on the tip shaping device.

In one embodiment, the tip shaping device may further be provided with a loop in which a finger may be inserted for better control. For example, the loop may be secured to the tip shaping device at the junction between the flap and the mandrel.

In one embodiment, the tip shaping device is made of at least one biocompatible and sterilizable material. Any adequate material may be used for the mandrel and the flap as long as the section of the flap adjacent to the mandrel is sufficiently flexible so as to be warp around at least a section of the lateral face of the mandrel. For example, both the mandrel and the flap may be made of the same material. In this case, the dimensions of the mandrel are chosen to provide rigidity for the mandrel and the dimensions of the flap are chosen to ensure that the flap be flexible. For example, the mandrel and the flap may be made of rubber, polymer, or the like. In another example, the mandrel and the flap are made of different materials. The mandrel may be made of a solid or rigid material such as metal while the flap may be made of a flexible material such as rubber, polymer or the like.

In one embodiment, the face of the flap that receives the guidewire may be coated with a hydrophilic, hydrophobic or friction-reducing coating.

In one embodiment, at least the flap may be made of transparent or translucent material so as to allow seeing the guidewire during the rotation of the mandrel and bending of the distal section of the guidewire.

In one embodiment, the above-described tip shaping tool is easy to use. The above-described tip shaping tool is also easy to fabricate and cost effective. Furthermore, the above-described tip shaping tool offers good shaping control over a variety of tip shapes, a good repeatability and prevents any damage to the guidewire.

The embodiments of the invention described above are intended to be exemplary only. The scope of the invention is therefore intended to be limited solely by the scope of the appended claims.

We claim:

1. A tip shaping device for shaping a tip of a guidewire, comprising:
   an elongated body extending along a longitudinal axis between two end faces and comprising a lateral face extending along the longitudinal axis between the two end faces;
   a planar body projecting from the lateral face of the elongated body, the planar body comprising a flexible section located adjacent to the elongated body and wrappable around at least a portion of the lateral face of the elongated body, the planar body comprising a guidewire receiving face adapted to shape the guidewire when received thereon and upon rotation of the elongated body about the longitudinal axis over the planar body; and
   a stopper body extending from the lateral face of the elongated body for limiting a rotation of the elongated body over the planar body.

2. The tip shaping device of claim 1, wherein the stopper body is provided with one of a square, rectangular and triangular cross-sectional shape.

3. The tip shaping device of claim 1, wherein a cross-sectional dimension of the elongated body varies along a longitudinal axis thereof.

4. The tip shaping device of claim 1, wherein a shape of the elongated body varies along a longitudinal axis thereof.

5. The tip shaping device of claim 1, wherein the guidewire receiving face is a face of the planar body that is in contact with the elongated body upon wrapping of the planar body over the elongated body.

6. The tip shaping device of claim 1, wherein the guidewire receiving surface is a lateral face.

7. The tip shaping device of claim 1, wherein the elongated and planar bodies are made of a biocompatible and sterilizable material.

8. The tip shaping device of claim 1, wherein the guidewire receiving face of the planar body is coated with one of a hydrophilic, hydrophobic and friction-reducing coating.

9. The tip shaping device of claim 1, wherein the elongated body is provided with one of a circular, an elliptical, a square, a rectangular, a hexagonal and a clothoid cross-sectional shape.

10. The tip shaping device of claim 1, further comprising a lever projecting from a lateral face of the elongated body for rotating the elongated body.

11. A tip shaping device for shaping a tip of a guidewire, comprising:
   an elongated body extending along a longitudinal axis between two end faces and comprising a lateral face extending along the longitudinal axis between the two end faces; and
   a planar body projecting from the lateral face of the elongated body, the planar body comprising a flexible section located adjacent to the elongated body and wrappable around at least a portion of the lateral face of the elongated body, the planar body comprising a guidewire receiving face adapted to shape the guidewire when received thereon and upon rotation of the elongated body about the longitudinal axis over the planar body; and
   wherein the planar body is provided with at least one groove on the guidewire receiving face for receiving the guidewire therein.

12. The tip shaping device of claim 11, wherein the elongated body is provided with at least one hole each facing a respective one of the at least one groove for receiving the guidewire therein.

13. The tip shaping device of claim 11, wherein the at least one groove is provided with groove ridges.

14. The tip shaping device of claim 11, wherein the elongated body is provided with at least one bump each extending along the lateral face thereof, each one of the at least one bump being aligned with a respective one of the at least one groove upon wrapping of the planar body over the elongated body.

15. The tip shaping device of claim 14, wherein the at least one bump is provided with bump ridges.

16. A tip shaping device for shaping a tip of a guidewire, comprising:
   an elongated body extending along a longitudinal axis between two end faces and comprising a lateral face extending along the longitudinal axis between the two end faces; and
   a planar body projecting from the lateral face of the elongated body, the planar body comprising a flexible section located adjacent to the elongated body and wrappable around at least a portion of the lateral face of the elongated body, the planar body comprising a guidewire receiving face adapted to shape the guidewire when received thereon and upon rotation of the elongated body about the longitudinal axis over the planar body; and
   wherein the lateral face of the elongated body is provided with at least one groove for receiving therein the guide wire.

17. The tip shaping device of claim 16, wherein the planar body is provided with at least one hole each facing a respective one of the at least one groove for receiving the guidewire therein.

18. The tip shaping device of claim 16, wherein the at least one groove is provided with groove ridges.

19. The tip shaping device of claim 16, wherein the planar body is provided with at least one bump each extending along the guidewire receiving face, each one of the at least one bump being aligned with a respective one of the at least one groove upon wrapping of the planar body over the elongated body.

20. The tip shaping device of claim 19, wherein the at least one bump is provided with bump ridges.

* * * * *